United States Patent [19]
Giordano et al.

[11] Patent Number: 5,198,557
[45] Date of Patent: Mar. 30, 1993

[54] PROCESS FOR THE RESOLUTION OF 3-(4-SUBSTITUTED-PHENYL)-GLYCIDIC ACID DERIVATIVES

[75] Inventors: Claudio Giordano, Monza; Roberto Casagrande, Bresso, both of Italy

[73] Assignee: Zambon Group S.p.A., Venice, Italy

[21] Appl. No.: 698,073

[22] Filed: May 10, 1991

[30] Foreign Application Priority Data

May 17, 1990 [IT] Italy .................. 20349 A/90

[51] Int. Cl.$^5$ .................. C07D 303/16; C07C 321/28
[52] U.S. Cl. .................. 549/513; 549/539; 562/401; 562/402; 560/17
[58] Field of Search .............. 562/402, 401; 549/513, 549/539; 560/17

[56] References Cited

U.S. PATENT DOCUMENTS

| | | | |
|---|---|---|---|
| 4,931,587 | 6/1990 | Piselli | 562/402 |
| 4,996,352 | 2/1991 | Mohacsi | 562/401 |

FOREIGN PATENT DOCUMENTS

| | | |
|---|---|---|
| 0059335 | 9/1982 | European Pat. Off. . |
| 0098892 | 1/1984 | European Pat. Off. . |
| 0127882 | 12/1984 | European Pat. Off. . |
| 0158340 | 10/1985 | European Pat. Off. . |
| 0343714 | 11/1989 | European Pat. Off. . |
| 0013775 | 1/1985 | Japan .................. 549/513 |
| 0013776 | 1/1985 | Japan .................. 549/513 |
| 1236467 | 6/1971 | United Kingdom . |
| 2130578 | 6/1984 | United Kingdom . |
| 2167063 | 5/1986 | United Kingdom . |
| 91/00270 | 1/1991 | World Int. Prop. O. . |

OTHER PUBLICATIONS

Merck Index, X Ed. No. 3189, p. 466.
Annual Drug Data Report, 1987, p. 507.
Protective Groups in Organic Synthesis, T. W. Green, Chapter 3, pp. 87–108.
J. Chem. Soc., Chem. Commun, 1990, vol (15), pp. 1018–1019 K. G. Watson et al., "Asymmetric Syntheses of (+) Diltiazem ...".

*Primary Examiner*—C. Warren Ivy
*Assistant Examiner*—Amelia A. Owens
*Attorney, Agent, or Firm*—Stevens, Davis, Miller & Mosher

[57] ABSTRACT

A process for the kinetic resolution of cis or trans enantiomeric mixtures of the compounds of formula

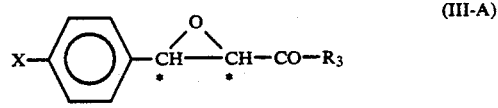

(III-A)

wherein $R_3$ and X have the meanings reported in the specification and the asterisks mark the asymmetric carbon atoms, is described.

The compounds of formula III-A are intermediates useful in the preparation of compounds active on the cardiovascular system.

8 Claims, No Drawings

PROCESS FOR THE RESOLUTION OF 3-(4-SUBSTITUTED-PHENYL)-GLYCIDIC ACID DERIVATIVES

The present invention relates to a process for the resolution of glycidic acid derivatives and, more particularly, it relates to a process for the resolution of 3-(4-substituted-phenyl)-glycidic acid derivatives such as esters or amides.

Ester as well as amide derivatives of 3-(4-methoxyphenyl)-glycidic acid are intermediates for the synthesis of compounds active on the cardiovascular system such as optically active 2,3-dihydro-2-(4-methoxyphenyl)-1,5-benzothiazepin-4(5H)-ones of formula

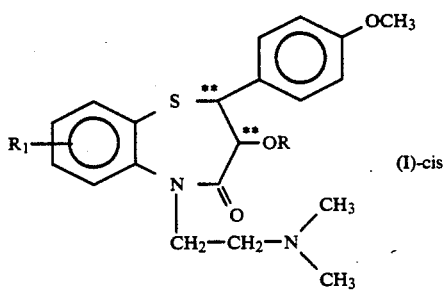

wherein
R represents a hydrogen atom or an acetyl group;
$R_1$ represents a hydrogen or chlorine atom;
the asterisks mark the asymmetric carbon atoms.

Specific examples of the compounds of formula I are Diltiazem, (+)-(2S,3S)-3-acetoxy-5-[2-(dimethylamino)-ethyl]-2,3-dihydro-2-(4-methoxyphenyl)-1,5-benzothiazepin-4(5H)-one (Merck Index, X Ed., No. 3189, page 466) and TA-3090, (+)-(2S,3S)-3-acetoxy-8-chloro-5-[2-(dimethylamino)-ethyl]-2,3-dihydro-2-(4-methoxyphenyl)-1,5-benzothiazepin-4(5H)-one (Annual Drug Data Report 1987, page 507).

Various methods for the preparation of the compounds of formula I are known in the literature such as for example those described in British patent No. 1,236,467, in European patent Nos. 127,882 and No. 158,340 and in the British patent application No. 2,167,063 all in the name of Tanabe Seiyaku Co. Ltd.

Most of these methods substantially foresee the following reaction scheme.

Scheme 1

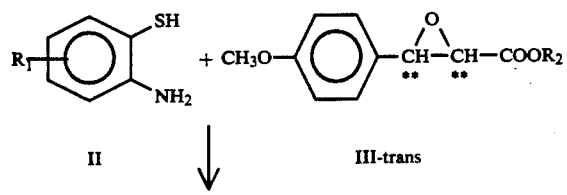

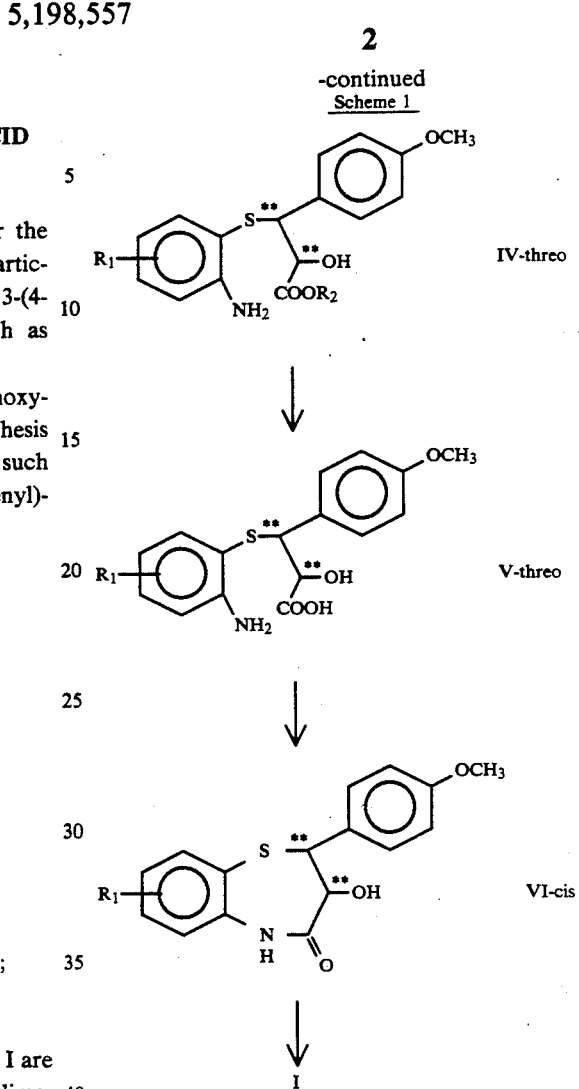

wherein $R_1$ represents a hydrogen or chlorine atom; $R_2$ represents a lower alkyl and the asterisks mark the asymmetric carbon atoms.

It has been also described a synthesis similar to that reported in scheme 1 in which a 2-nitro-thiophenol is used instead of Compound II and the nitro group of the condensation product is reduced to amino group before the cyclization reaction (European patent No. 59,335—Tanabe Seiyaku Co. Ltd.).

Each of these methods necessarily foresees an optical resolution step, generally at the level of an intermediate of the synthesis, in order to separate the enantiomer with the desired configuration.

In fact, there are known the resolution of the cyclic intermediate of formula VI by 1-(2-naphthylsulphonyl)-pyrrolidine-2-carbonyl chloride, described in the above cited British patent application No. 2,167,063 and the resolution of the intermediate of formula V by optically active bases such as 4-hydroxyphenyl-glycine methyl ester and cinchonidine, described in the above cited European patent No. 127,882, by α-phenethylamine, described in the European patent No. 98,892 (Tanabe Seiyaku Co. Ltd.) and by L-lysine, described in the British patent No. 2,130,578 (Istituto Luso Farmaco).

It is clear to the man skilled in the art that a resolution at an earlier step of the synthesis, that is at the level of glycidic intermediate III, is surely interesting.

Recently, an enzymatic resolution of esters of formula III ($R_2$=lower alkyl) has been described (European patent application No. 343,714—Stamicarbon B.V.).

However, enzymatic resolutions are seldom economically more advantageous than chemical resolutions because the enzyme, which may have a high cost, must be recovered and it loses its specific activity in time.

Chemical resolutions have been described at the level of free acid III ($R_2$=H) by using an optically active base which affords diastereoisomeric salts. However, in this specific case, such a resolution is particularly laborious and difficult because of the instability of free acid III ($R_2$=H).

We have found a kinetic resolution process which allows to obtain the compounds of formula III or their precursors with a high enantiomeric purity starting from mixtures of cis enantiomers (2S,3S and 2R,3R) as well as of trans enantiomers (2R,3S and 2S,3R).

Therefore, object of the present invention is a process for the kinetic resolution of mixtures of cis or trans enantiomers of the compounds of formula

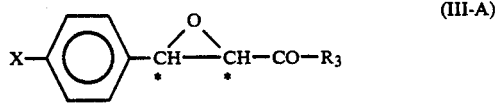

(III-A)

wherein $R_3$ represents a linear or branched $C_1$–$C_{18}$ alkoxy group, a benzyloxy or an amino, mono or dialkylamino group in which the alkyl moiety has from 1 to 6 carbon atoms;

X represents a methoxy group or a group transformable into a methoxy group selected among the group consisting of hydroxy and hydroxy protected as benzyloxy or as an ester with an acid usually used for protecting phenols;

the asterisks mark the asymmetric carbon atoms;

comprising the reaction between a racemic mixture of cis or trans enantiomers of the compounds of formula III-A with a thiophenol of formula

(II-A)

wherein $R_4$ and $R_5$, the same or different, represent hydrogen or chlorine atoms, $C_1$–$C_4$ alkyl, amino, acetylamino and nitro groups;

in the presence of a catalytic amount of an optically active tertiary amine in an inert solvent and at a temperature between −20° C. and +30° C.

The above process consists in a kinetic resolution since, under the above reported conditions, one of the two enantiomers reacts with thiophenol II-A faster than the other in order to give a compound of formula

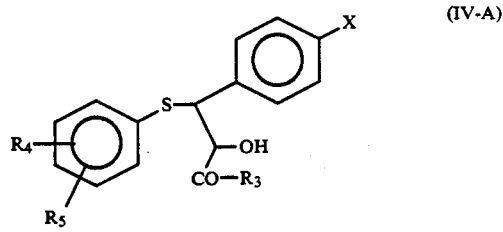

(IV-A)

wherein $R_3$, $R_4$, $R_5$ and X have the above reported meanings;

which derives from a trans-type opening of the epoxy ring.

By quenching the reaction at about 50% conversion, the other enantiomer remains in solution in an unreacted form and with a high enantiomeric purity.

It is the nature of the optically active tertiary amine to determine which of the two enantiomers reacts faster.

Although the reaction mechanism has not been yet explained, our experimental observations suggest that the reaction runs through an attack of an ammonium thiophenate (obtained in situ by reaction of thiophenol II-A with the optically active tertiary amine) on the epoxy ring of compound III-A with trans opening of the ring.

Since the first reaction in scheme 1 can be carried out through a cis opening (in basic environment) as well as through a trans opening (thermic) of the epoxide, it is clear that the present process is particularly advantageous because, in addition to the good results of the kinetic resolution, it allows to use compounds III-A with cis configuration for the synthesis of the compounds of formula I.

In fact, as above reported, the selection of the optically active tertiary amine determines which of the two enantiomers of compounds III-A reacts faster.

For example, starting from a mixture of trans enantiomers III-A (2R,3S and 2S,3R) it is possible to carry out the reaction on the (2S,3R) enantiomer preferentially while keeping unchanged the (2R,3S) enantiomer which, by thermic condensation with 2-amino-thiophenol, directly gives the compound IV of scheme 1 in the right configuration.

Analogously, starting from racemic cis-compound III-A, the kinetic resolution gives (2R,3R) enantiomer III-A which, by subsequent reaction with 2-amino-thiophenol in basic environment, gives the intermediate IV of scheme 1 in the right configuration.

On the contrary, if the process of the invention is carried out under conditions in which the reaction is faster on (2R,3R) enantiomer III-A, the use of 2-aminothiophenol as compound of formula II-A directly gives the compound IV of scheme 1 in the right configuration.

It is clear that, what above reported, can be carried out according to a procedure similar to that reported in scheme 1, by using, when it is appropriate, 2-nitro-thiophenol, so obtaining an intermediate of formula IV wherein a nitro group instead of the amino group is present.

The critical factors and the parameters of the process object of the present invention are herein below reported.

Substrate: (compounds of formula III-A)

As above reported, the process is suitable to be carried out on racemic mixtures of cis as well as trans enantiomers III-A.

The two substrates (cis or trans mixtures) are equivalent and this is an advantage since it allows to use also cis enantiomers III-A in the synthesis of the compounds of formula I.

As far as the substituents of the compounds of formula III-A are concerned, the usefulness of having the carboxy group in the form of an ester with alcohols having a low as well as a high number of carbon atoms or in the form of an amide lies in the consequent possibility of modulating the lipophilicity of compound III-A as a function of the other reaction parameters.

Substituent X can also be selected dependent upon several factors such as for example the possibility of modulating the lipophilicity of compound III-A. For this purpose suitably protected hydroxy group can be used.

For a comprehensive reference to the protection of phenols and their deprotection see Theodora W. Green—Protective Groups in Organic Synthesis—Chapter 3, pages 87–108—John Wiley & Sons.

Obviously, the preferred substituent X is methoxy because it is the substituent present in the compounds of formula I.

Reagent

Specific examples of the thiophenols of formula II-A are thiophenol, 4-methyl-thiophenol, 4-isopropyl-thiophenol, 4-tert.butyl-thiophenol, 2-amino-thiophenol, 2-nitro-thiophenol, 2-amino-5-chloro-thiophenol, 2-nitro-5-chloro-thiophenol, 2,4-dimethyl-thiophenol, 2,6-dimethyl-thiophenol.

The selection among the thiophenols of formula II-A depends on the kind of reaction to be carried out and, in particular, it depends if the purpose of the reaction is to obtain an unreacted enantiomer III-A with high purity (for example the 2R, 3S enantiomer) or directly a product of formula IV (scheme 1).

In the first case the reaction will be carried out between the racemic mixture and any suitable thiophenol II-A while in the second case 2-amino-thiophenol, 2-nitro-thiophenol, 2-amino-5-chloro-thiophenol or 2-nitro-5-chloro-thiophenol will be used only.

The amount of thiophenol II-A to be used is between 0.4 and 3 moles by mole of the substrate.

Since it is not wanted that the reaction runs with a conversion higher than 50% (in order to avoid the reaction of the second enantiomer after the first enantiomer) and compound II-A can be also used in excess (more than 50% as molar amount) with respect to substrate III-A, the course of the reaction must be followed so that the reaction is quenched as soon as the desired conversion is reached.

Generally, it is preferred to use an amount of thiophenol II-A between 0.4 and 1 mole by mole of substrate and it is still more preferred to use an amount between 0.5 and 0.7 moles of compound II-A by mole of compound III-A.

Catalyst

Examples of optically active tertiary amines useful for the process of the invention are optically active cinchona bases, N,N-dialkyl-ephedrines, dialkyl-phenylamines, $\alpha$- or $\beta$-hydroxy-trialkylamines.

Cinchona bases such as cinchonine, dihydrocinchonidine, quinine, quinidine and cinchonidine are preferred.

Among the cinchona bases, cinchonidine is the most preferred one.

Quaternary ammonium salts of the above bases can be used too, optionally in the presence of another base.

When cinchonidine is used together with, for example, racemic trans III-A, the 2S,3R enantiomer reacts while the desired 2R,3S enantiomer remains substantially unchanged in solution, obviously by quenching the reaction at about 50% conversion.

The molar amount of catalyst to be used is between 3 and 50% with respect to compound III-A, preferably between 10 and 50%.

The tertiary amine can be recovered practically quantitatively at the end of the reaction.

Solvent

It is preferred to dissolve compound II-A in the reaction medium, but it is not necessary that substrate III-A and the tertiary amine are completely dissolved.

Then, suitable solvents are those inert under the reaction conditions and able to dissolve compound II-A as well as, at least partially, substrate III-A and the tertiary amine.

Examples of preferred solvents are benzene, toluene, o-xylene, m-xylene, p-xylene, chlorobenzene, o-dichlorobenzene, m-dichlorobenzene, p-dichlorobenzene or mixtures thereof.

Temperature

The preferred temperature range is between $-20°$ C. and $30°$ C. By working below $-20°$ C., the reaction runs too slowly from an industrial point of view even if it provides the desired results.

On the contrary, at temperatures above $30°$ C., the selectivity required in order to carry out the kinetic resolution object of the invention is partially lost.

Within the preferred temperatures, the desired degree of conversion (50%) is reached in some hours (about 4–24 hours).

A practical embodiment of the process object of the present invention consists in reacting a mixture of compound III-A, compound II-A and the optically active tertiary amine in an inert solvent, for example an aromatic solvent, at the selected temperature.

The course of the reaction is followed and, when the desired degree of conversion is reached (about 50% of compound III-A), the reaction is quenched by pouring the reaction mixture into an aqueous acid.

The optically active tertiary amine, which is recycled, is recovered from the aqueous layer.

From the organic layer, unreacted enantiomer III-A is separated from reaction product IV-A.

If compound IV-A has the desired configuration, it is further transformed as described in scheme 1 in order to obtain the corresponding compound of formula I.

On the contrary, if the unreacted enantiomer III-A has the right configuration, it is reacted with 2-amino-thiophenol (or 2-nitrothiophenol) according to scheme 1.

The enantiomeric purity of the obtained product or of the unreacted enantiomer is high and, therefore, the usual work-up in the subsequent steps of the process for the synthesis of the compounds of formula I (for example scheme 1) allows to obtain the desired final products with an optical purity according to Pharmacopoeia requirements, without further optical separations.

Therefore, the process object of the present invention shows several advantages which are useful from an industrial point of view.

In fact, as far as we know, the process of the invention is the first example of not-enzymatic kinetic resolution to separate the enantiomers of formula III-A and it allows to carry out the optical separation in the first step of the process for the synthesis of the compounds of formula I. In addition, the practical realization of the process of the invention is simple and it does not require any particular reaction condition or equipment; the optically active tertiary amine is easily recovered and recycled.

In order to better illustrate the present invention the following examples are now given.

EXAMPLE 1

Cinchonidine (1.5 g; 5 mmol) and, then, 2-amino-thiophenol (0.62 g; 5 mmol) were added, under stirring at 20° C., to a solution of racemic trans-3-(4-methoxyphenyl)-glycidic acid methyl ester (2 g; 10 mmol) in toluene (20 ml).

The reaction mixture was kept under stirring at 20° C. for 20 hours and poured under stirring into 1N hydrochloric acid solution (20 ml).

The phases were separated and the aqueous phase was extracted with methylene chloride (20 ml).

The collected organic phases were washed with water (20 ml) and dried on sodium sulfate.

The evaporation of the solvent under vacuum gives a crude compound containing, according to HPLC and $^1$H-NMR analysis, (2R,3S)-trans-3-(4-methoxyphenyl)-glycidic acid methyl ester (0.95 g).

The ester was isolated by chromatography on silica gel using a mixture n.hexane:ethyl ether=8:2 as eluent.

(2R,3S)-3-(4-methoxyphenyl)-glycidic acid methyl ester (0.6 g) with a 60% enantiomeric excess was obtained.

Then, the methyl ester was dissolved in toluene (4.2 ml).

2-amino-thiophenol (0.36 g; 2.88 mmol) was added to the solution, the mixture was heated under reflux for 2 hours and, then, cooled to room temperature.

The insoluble residue was filtered off and dried under vacuum in oven.

(2S,3S)-2-hydroxy-3-(2-aminophenylthio)-3-(4-methoxyphenyl)-propionic acid methyl ester with 72% enantiomeric purity ($[\alpha]_D^{20} = +72°$—c=0.5% CHCl$_3$) was obtained. The enantiomeric purity by HPLC with chiral columns was 80%.

EXAMPLE 2

Cinchonidine (3.7 g; 12.6 mmol) and, then, 2-amino-thiophenol (2.4 g; 19 mmol) were added, under stirring and under nitrogen at 0° C., to a solution of racemic trans-3-(4-methoxyphenyl)-glycidic acid methyl ester (8 g; 38 mmol) in toluene (80 ml).

The reaction mixture was kept under stirring at 0° C. for 24 hours and poured under stirring into 1N hydrochloric acid solution (80 ml).

The phases were separated and the aqueous phase was extracted with methylene chloride (80 ml).

The collected organic phases were washed with water (80 ml) and dried on sodium sulfate.

The HPLC analysis (chiral column) of the solution was carried out. The solution contained trans-3-(4-methoxyphenyl)-glycidic acid methyl ester (4.72 g; 22.7 mmol) with a ratio (2R,3S):(2S,3R)=73:27.

EXAMPLE 3

Cinchonidine (2.82 g; 9.6 mmol) and, then, 2-amino-thiophenol (1.68 g; 13.44 mmol) were added, under stirring and under nitrogen at 0° C., to a solution of racemic trans-3-(4-methoxyphenyl)-glycidic acid methyl ester (4 g; 19.2 mmol) in toluene (40 ml).

The reaction mixture was kept under stirring at 0° C. for 24 hours and poured under stirring into 1N hydrochloric acid solution (40 ml). The phases were separated and the aqueous phase was extracted with methylene chloride (40 ml).

The collected organic phases were washed with water (40 ml) and dried on sodium sulfate.

The HPLC analysis (chiral column) of the solution was carried out.

The solution contained trans-3-(4-methoxyphenyl)-glycidic acid methyl ester (1.6 g; 7.7 mmol) with a ratio (2R,3S):(2S,3R)=85:15.

What we claim is:

1. A process for the kinetic resolution of mixtures of cis or trans enantiomers of the compounds of formula

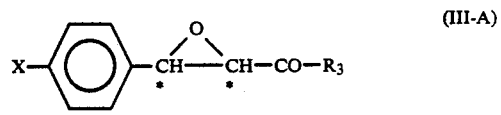

(III-A)

wherein

R$_3$ represents a linear or branched C$_1$–C$_{18}$ alkoxy group, a benzyloxy or an amino, mono or dialkylamino group in which the alkyl moiety has from 1 to 6 carbon atoms;

X represents a methoxy group or a group transformable into a methoxy group selected from the group consisting of hydroxy and hydroxy protected as benzyloxy or as an ester with an acid adapted for protecting phenols;

the asterisks mark the asymmetric carbon atoms;

comprising the reaction between a racemic mixture or cis or trans enantiomers of the compounds of formula III-A with a thiophenol of formula

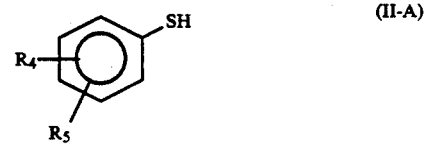

(II-A)

wherein

R$_4$ and R$_5$, the same or different, represent hydrogen or chlorine atoms, C$_1$–C$_4$ alkyl, amino, acetylamino and nitro groups;

in the presence of a catalytic amount of an optically active tertiary amine in an inert solvent and at a temperature between −20° C. and +30° C., said process allowing one to obtain both (a) one of the two enantiomers of each couple cis or trans of the compounds of formula (III-A), remained unreacted in solution in high enantiomeric purity, and (b) one compound of formula (IV-A)

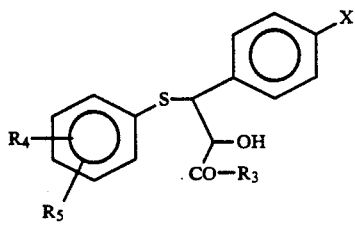

(IV-A)

wherein $R_3$, $R_4$, $R_5$ and X have the above meanings, which is the product of the above reaction.

2. A process according to claim 1 in which, when the molar amount of thiophenol II-A is higher than 50% with respect to compound III-A, the reaction is quenched at about 50% conversion of compound III-A.

3. A process according to claim 1 in which the thiophenol of formula II-A is selected from the group consisting of thiophenol, 4-methyl-thiophenol, 4-isopropyl-thiophenol, 4-tert.butyl-thiophenol, 2-amino-thiophenol, 2-nitro-thiophenol, 2-amino-5-chloro-thiophenol, 2-nitro-5-chloro-thiophenol, 2,4-dimethyl-thiophenol, and 2,6-dimethyl-thiophenol.

4. A process according to claim 1 in which the optically active tertiary amine is selected from the group consisting of N,N-dialkyl-ephedrines, dialkylphenylamines, α- or β-hydroxy-trialkylamines, cinchonine, dihydrocinchonidine, quinine, quinidine, chinchonidine and quaternary ammonium salts thereof.

5. A process according to claim 1 in which the optically active tertiary amine is cinchonidine.

6. A process according to claim 1 in which the molar amount of the optically active tertiary amine is between 3 and 50% with respect to compound III-A.

7. A process according to claim 1 in which the solvent is selected from the group consisting of benzene, toluene, o-xylene, m-xylene, p-xylene, chlorobenzene, o-dichlorobenzene, m-dichlorobenzene, p-dichlorobenzene and mixtures thereof.

8. A process according to claim 1 comprising the reaction of a mixture of compound III-A, compound II-A and an optically active tertiary amine in an inert solvent at the selected temperature, the quenching of the reaction at 50% degree of conversion of compound III-A, and the separation of unreacted compound III-A from compound IV-A.

* * * * *